United States Patent
Daifuku

(10) Patent No.: US 10,071,112 B2
(45) Date of Patent: Sep. 11, 2018

(54) VITAMIN E-NUCLEOSIDE PRODRUGS

(71) Applicant: EPIGENETICS PHARMA LLC, Mercer Island, WA (US)

(72) Inventor: Richard Daifuku, Mercer Island, WA (US)

(73) Assignee: Epigenetics Pharma LLC, Mercier Island, WA (US)

( * ) Notice: Subject to any disclaimer, the term of this patent is extended or adjusted under 35 U.S.C. 154(b) by 0 days.

(21) Appl. No.: 15/516,657

(22) PCT Filed: Oct. 8, 2015

(86) PCT No.: PCT/US2015/054752
§ 371 (c)(1),
(2) Date: Apr. 3, 2017

(87) PCT Pub. No.: WO2016/057825
PCT Pub. Date: Apr. 14, 2016

(65) Prior Publication Data
US 2017/0298088 A1     Oct. 19, 2017

Related U.S. Application Data

(60) Provisional application No. 62/061,471, filed on Oct. 8, 2014.

(51) Int. Cl.
| | |
|---|---|
| *C07H 19/10* | (2006.01) |
| *C07H 19/20* | (2006.01) |
| *A61K 31/7068* | (2006.01) |
| *A61K 47/54* | (2017.01) |
| *A61K 47/55* | (2017.01) |
| *A61K 31/355* | (2006.01) |
| *A61K 47/48* | (2006.01) |

(52) U.S. Cl.
CPC ........ *A61K 31/7068* (2013.01); *A61K 31/355* (2013.01); *A61K 47/48061* (2013.01); *A61K 47/48092* (2013.01); *A61K 47/48107* (2013.01); *A61K 47/549* (2017.08); *A61K 47/55* (2017.08); *C07H 19/10* (2013.01); *C07H 19/20* (2013.01)

(58) Field of Classification Search
None
See application file for complete search history.

(56) References Cited

U.S. PATENT DOCUMENTS

| | | |
|---|---|---|
| 6,384,019 B1 | 5/2002 | Myhren et al. |
| 7,223,770 B2 | 5/2007 | Zhang et al. |
| 7,601,703 B2 | 10/2009 | Shepard et al. |
| 8,552,054 B2 | 10/2013 | Swindell et al. |
| 8,716,445 B2 | 5/2014 | Lal et al. |
| 2005/0096340 A1 | 5/2005 | Zhang |
| 2011/0280949 A1 | 11/2011 | Malaya et al. |
| 2013/0296345 A1 | 11/2013 | Quart |

FOREIGN PATENT DOCUMENTS

| | | | |
|---|---|---|---|
| CN | 103130854 A | 6/2013 | |
| DE | 2111856 A1 | 9/1972 | |
| EP | 0226753 A2 * | 7/1987 | ............. C07H 19/10 |
| EP | 0226753 B1 | 4/1991 | |
| JP | S62145019 A | 6/1987 | |
| WO | 1992/013522 A1 | 8/1992 | |
| WO | WO 2006/029081 A2 | 3/2006 | |

OTHER PUBLICATIONS

Alexander, RL et al., "A novel phospholipid gemcitabine conjugate is able to bypass three drug-resistance mechanisms". Cancer Chemotherapy Pharmacol., Jul. 2005, vol. 56, Issue 1, pp. 15-21 [online] [retrieved on Apr. 13, 2017] from the internet <URL: http://link.springer.com/article/10.1007/s00280-004-0949-0#/page-1>;abstract.

Extended European Search Report for EP Application No. 15848354.5, titled: "Vitamin E-Nucleoside Prodrugs," dated Apr. 30, 2018.

Husain, K. et al., "Vitamin E δ-Tocotrienol Augments the Anti-Tumor Activity of Gemcitabine and Suppresses Constructive NF-kB Activation in Pancreatic Cancer," Mol. Cancer Ther., vol. 10; No. 2; 2363-2372 (2011).

\* cited by examiner

*Primary Examiner* — Traviss C McIntosh, III
(74) *Attorney, Agent, or Firm* — Hamilton, Brook, Smith & Reynolds, P.C.

(57) ABSTRACT

The present disclosure describes nucleoside and nucleoside analogs that are conjugated to a vitamin E derivative via a phosphate ester or a phosphoramidate linkage. The nucleoside or nucleoside analogs can provide enhanced therapeutic activity (e.g., antiproliferative activity against tumor cells) and/or greater chemical stability in aqueous solutions.

15 Claims, No Drawings

VITAMIN E-NUCLEOSIDE PRODRUGS

CROSS-REFERENCE TO RELATED APPLICATION

This application is the U.S. National Stage of International Application No. PCT/US2015/054752, filed Oct. 8, 2015, which designates the U.S., published in English, and claims the benefit of provisional application 62/061,471, filed Oct. 8, 2014. The entire teachings of the above applications are incorporated herein by reference.

BACKGROUND

A major hurdle in the realm of pharmaceutical and medicinal chemistry is the ability to deliver biologically effective drugs that are soluble in a carrier and chemically stable when presented to an aqueous environment. One way to solubilize and stabilize medicinal agents is to chemically modify them or conjugate them to another molecule to alter the solubility profile and chemical stability in a particular solvent. Conjugates of active drugs, often referred to as prodrugs, include chemical derivatives of biologically-active parent compounds that are converted into the parent compounds in vivo. The release of the active parent drug from the prodrug conjugate may occur as the result of processes such as hydrolysis or enzymatic cleavage. The rate of release is influenced by several factors, including the type of chemical bond joining the active parent drug to the conjugate moiety.

Several technologies have been developed to facilitate the delivery of poorly soluble and insoluble compounds to patients. Examples of technologies specifically designed to solve solubility problems include complexing agents, nanoparticles, microemulsions, solubility enhancing formulations, prodrugs, and novel polymer systems. As a specific example, a water-soluble moiety (e.g., polyethylene glycol, polyglutamate, or polymer) can be conjugated to a drug to increase solubility and circulation life.

5-azacytidine is a chemical analogue of cytidine with antineoplastic activity. 5-azacytidine is unstable in buffer and plasma, with an average terminal half-life of 1.50±2.30 hours in clinical plasma samples. In vitro, a 20% loss of 5-azacytidine occurs even at −60° C. after 4.5 days storage, and a 10% loss occurs within 0.5 hours when stored at room temperature.

An elaidic ester of 5-azacytidine has been developed in an effort to improve chemical stability of 5-azacytidine. The ester prodrug can be made by conjugating elaidic acid to the 5' position of the sugar of 5-azacytidine. 5-azacytidine elaidic acid esters have a significantly better plasma stability profile than 5-azacytidine itself. For example, when held in blank human plasma matrix at room temperature for at least 4 hours under the experimental conditions, 94% percent of the initial 5-azacytidine elaidic acid ester can remain (compared to an initial amount) with no significant degradation products in the post-extract supernatant, after precipitation of plasma proteins. Furthermore, the ring-opening of the 5-azacytidine-moiety or other degradation of the compound is significantly reduced when the elaidic acid side chain is attached to 5-azacytidine.

In addition to providing chemical stability, conjugation of 5-azacytidine with elaidic acid can bypass the transport mechanism for nucleosides, which can be one source for drug resistance. The elaidic acid ester conjugate can also reduce the likelihood of deamination by cytidinedeaminase.

Similarly, an elaidic acid ester prodrug of gemcitabine has also been previously developed. However, clinical trials did not show any difference in survival in patients with pancreatic cancer between the elaidic acid prodrug and gemcitabine.

Vitamin E presents another method for functionalizing therapeutic agents. There are two main forms of vitamin E: tocopherols and tocotrienols. Tocotrienols represent a very important part of the vitamin E family. However, most of the vitamin E research has focused on α-tocopherols, and only 1% of vitamin E studies have investigated tocotrienols.

Some of the isoforms of tocopherols and tocotrienols have been reported to have antiproliferative activity. Indeed, tocotrienols have shown an activity against a number of different cancers, including breast, leukemia, liver, pancreas, and prostate, amongst others. It should be noted that γ-tocotrienol appears to be the most frequently tested for antineoplastic activity, but that formal ranking of relative biopotency of tocopherols and tocotrienols for suppression of cell growth and induction of cell death of specific vitamin E isoforms display a consistent relationship corresponding to δ-tocotrienol≥γ-tocotrienol>α-tocotrienol>δ-tocopherol>>γ and α-tocopherol.

α-Tocopheryl phosphate (α-TP), a water-soluble analogue of α-tocopherol, is found in humans, animals, and plants. α-TP is resistant to both acid and alkaline hydrolysis and may exert its own function in this form in vivo. α-TP appears to be taken in and hydrolyzed readily to α-tocopherol in cultured cells and in mice. This hydrolysis of α-TP to α-tocopherol most likely is mediated by a phosphatase. α-TP has been found to be pro-apoptotic and mixed tocopheryl phosphates have shown little toxicity in formal toxicology studies.

Nucleosides typically need to be metabolized to nucleotides, i.e., phosphorylated nucleosides, to be effective as therapeutics. A rate limiting step in nucleotide synthesis is generation of the monophosphate (MP). For example, gemcitabine is phosphorylated to the MP by deoxycytidine kinase (dCK) and dCK "deficiency" can be responsible for acquired and intrinsic resistance. While desirable, delivery of MP-nucleosides to cells has been a challenge in medicinal chemistry because phosphates are acidic and negatively charged at physiologic pH, and phosphohydrolases rapidly convert MP-nucleosides to corresponding nucleosides. Furthermore, because many nucleosides are poorly phosphorylated, intracellular delivery of a monophosphorylated nucleoside with low toxicity and good affinity to polymerases is a challenge that has been difficult to surmount.

There is a need for therapeutic agents that can bypass major mechanisms of tumor resistance while providing enhanced stability and activity. The present disclosure seeks to fulfill this need and provides further related advantages.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the present disclosure provides, inter alia, compounds according to Formula (I):

Y-L-Nu       (I)

wherein Y is a tocopherol moiety or a tocotrienol moiety;
L is a phosphate ester or phosphoramidate linker; and Nu is selected from a purine nucleoside, a pyrimidine nucleoside, an azapyrimidine nucleoside, and a nucleoside analogue.

In another aspect, the present disclosure provides, inter alia, compounds according to Formula (II):

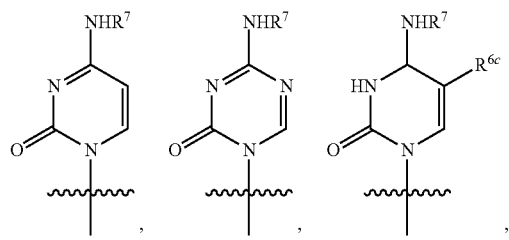

or a pharmaceutically acceptable salt thereof, wherein:
$R^1$ is selected from:

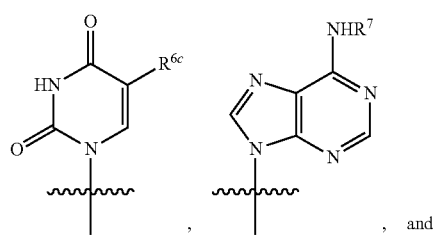, and

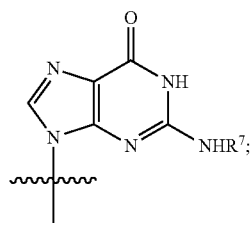

$R^2$ and $R^3$ are each independently selected from H, halo, and OH, provided that $R^2$ and $R^3$ cannot both be OH;

$R^{6a}$ is selected from absent, H and $C_{1-6}$ alkyl;

W is O or $NR^{6b}$, $R^{6b}$ is selected from H, $C_{1-6}$ alkyl, $C_{1-6}$ alkoxy, wherein said $C_{1-6}$ alkyl and $C_{1-6}$ alkoxy are each optionally substituted with 1 or 2 substituents independently selected from aryl and heteroaryl, wherein said aryl or heteroaryl is optionally substituted with 1 or 2 substituents independently selected from cyano and nitro, $R^{6c}$ is selected from H, $C_{1-6}$ alkyl, and $C_{1-6}$ haloalkyl;
$R^7$ is H or $C_{1-6}$ alkyl; and
X is

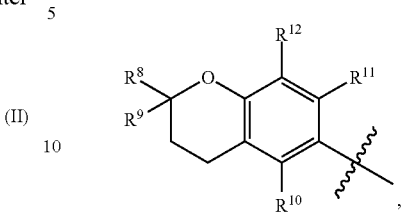

wherein
$R^8$ is selected from $C_{12-24}$ alkyl, $C_{12-24}$ alkenyl, $C_{12-24}$ haloalkyl, and $C_{12-24}$ haloalkenyl,
$R^9$, $R^{10}$, $R^{11}$, and $R^{12}$ are each independently selected from H, $C_{1-6}$ alkyl, and halo.

In yet another aspect, the present disclosure provides compositions including a compound of Formula (I) or (II).

In yet another aspect, the present disclosure provides methods for intracellular delivery of a monophosphorylated nucleoside or nucleoside analogue, including contacting a cell with a compound of Formula (I) or (II).

In yet another aspect, the present disclosure provides methods for bypassing nucleoside transport mechanisms, including contacting a cell with a compound of any one of Formula (I) or (II).

In yet another aspect, the present disclosure provides methods for improving a circulatory half-life of a nucleoside or a nucleoside analogue, including covalently attaching (i.e., covalently coupling) the nucleoside or the nucleoside analogue to α-tocopheryl, β-tocopheryl, γ-tocopheryl, δ-tocopheryl, α-tocotrienyl, β-tocotrienyl, γ-tocotrienyl, or δ-tocotrienyl.

In yet another aspect, the present disclosure provides methods of treating a disease in a patient (e.g., a cancer, such as breast, lung, or colon cancer), including administering to the patient a therapeutically effective amount of a compound of Formula (I) or (II).

DETAILED DESCRIPTION

The present disclosure describes nucleoside and nucleoside analogues that are conjugated to a vitamin E derivative via a phosphate ester or a phosphoramidate linkage. Without wishing to be bound by theory, it is believed that vitamin E-conjugated nucleoside and nucleoside analogues of the present disclosure can intracellularly deliver a MP-nucleoside or a MP-nucleoside analogue, while bypassing a rate-limiting step in nucleotide synthesis and a mechanism of nucleoside resistance.

The compounds of the present disclosure have numerous advantages. For example, nucleoside and nucleoside analogues that are conjugated to vitamin E derivatives can have an enhanced anticancer activity due to the vitamin E derivatives. The compounds of the present disclosure also overcome two major mechanisms of tumor resistance to nucleosides (a) nucleoside transport and (2) downregulation of monophosphorylation, which can be more important. The vitamin E-modified nucleoside and nucleoside analogues can improve a bioavailability (e.g., oral bioavailability) of a parent unmodified nucleoside or nucleoside analogue that otherwise has poor oral bioavailability. In some embodiments, the compounds of the present disclosure are soluble in a hydrophobic matrix for preferential uptake of the nucleoside in tumors due to enhanced permeability and retention. Furthermore, the nucleoside or nucleoside analogues can provide greater chemical stability in aqueous solutions and/or enhanced therapeutic activity (e.g., antiproliferative activity against tumor cells). In some embodiments, the vitamin E-modified nucleoside or nucleoside analogues can increase the circulatory half-life of the nucleoside or nucleoside analogues.

In some embodiments, the compounds have a general Formula (I)

$$Y\text{-}L\text{-}Nu \qquad (I)$$

wherein Y is a tocopherol moiety or a tocotrienol moiety;
L is a phosphate ester or phosphoramidate linker; and
Nu is selected from a purine nucleoside, a pyrimidine nucleoside, an azapyrimidine nucleoside, and a nucleoside analogue.

In some embodiments, Y is a vitamin E moiety. For example, Y can be tocopherol moiety. In some embodiments, Y is a tocotrienol moiety.

In some embodiments, Nu is a pyrimidine nucleoside.
In some embodiments, Nu is a purine nucleoside.
In some embodiments, Nu is an azapyrimidine nucleoside (e.g., 5-azacytidine, 5-azadeoxycytidine, or 2',2'-difluoro-5-azadeoxycytidine).

In some embodiments, Nu is a nucleoside analogue.
In some embodiments, the compound has Formula (II):

(II)

or a pharmaceutically acceptable salt thereof, wherein:
$R^1$ is $R^2$ and $R^3$ are each independently selected from H, halo, and OH, provided that $R^2$ and $R^3$ cannot both be OH;

$R^{6a}$ is selected from absent, H and $C_{1-6}$ alkyl;
W is O or $NR^{6b}$,
$R^{6b}$ is selected from H, $C_{1-6}$ alkyl, $C_{1-6}$ alkoxy, wherein said $C_{1-6}$ alkyl and $C_{1-6}$ alkoxy are each optionally substituted with 1 or 2 substituents independently selected from aryl and heteroaryl, wherein said aryl or heteroaryl is optionally substituted with 1 or 2 substituents independently selected from cyano and nitro,
$R^{6c}$ is selected from H, $C_{1-6}$ alkyl, and $C_{1-6}$ haloalkyl;
$R^7$ is H or $C_{1-6}$ alkyl; and
X is wherein
$R^8$ is selected from $C_{12-24}$ alkyl, $C_{12-24}$ alkenyl, $C_{12-24}$ haloalkyl, and $C_{12-24}$ haloalkenyl, and
$R^9$, $R^{10}$, $R^{11}$, and $R^{12}$ are each independently selected from H, $C_{1-6}$ alkyl, and halo.

In some embodiments, $R^1$ is

In some embodiments, $R^1$ is

In some embodiments, $R^1$ is

In some embodiments, $R^1$ is

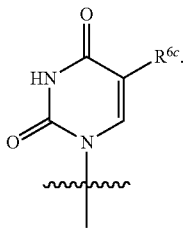

In some embodiments, $R^1$ is

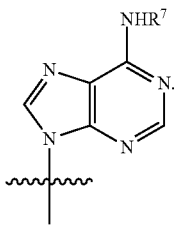

In some embodiments, $R^1$ is

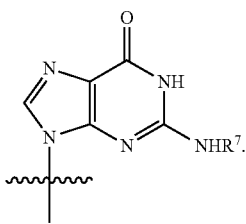

In some embodiments, $R^2$ and $R^3$ are each F.
In some embodiments, $R^2$ and $R^3$ are each independently selected from H, halo, and OH, provided that $R^2$ and $R^3$ cannot both be OH, and provided that $R^2$ and $R^3$ cannot both be H.
In some embodiments, W is O.
In some embodiments, W is $NR^{6b}$.
In some embodiments, $R^{6b}$ is H or $C_{1-6}$ alkyl.
In some embodiments, $R^{6c}$ is methyl or trifluoromethyl.
In some embodiments, $R^{6a}$ is absent.
In some embodiments, when $R^{6a}$ is absent, W is O.
In some embodiments, $R^{6a}$ is absent or H.
In some embodiments, $R^{6a}$ is absent or $C_{1-6}$ alkyl.
It is understood that when $R^{6a}$ is absent, the adjacent oxygen is negatively charged (i.e.,

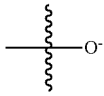

).
In some embodiments, $R^{6a}$ is H or $C_{1-6}$ alkyl.
In some embodiments, $R^{6a}$ is H, methyl, or ethyl.
In some embodiments, $R^{6a}$ is H or methyl.
In some embodiments, $R^{6a}$, $R^{6b}$, and $R^{6c}$ are each independently H, methyl, or ethyl.
In some embodiments, $R^{6a}$, $R^{6b}$, and $R^{6c}$ are each independently H or methyl.
In some embodiments, $R^{6a}$, $R^{6b}$, and $R^{6c}$ are each H.
In some embodiments, $R^7$ is H, methyl, or ethyl.
In some embodiments, $R^7$ is H or methyl.
In some embodiments, $R^7$ is H.
In some embodiments, $R^9$, $R^{10}$, $R^{11}$, and $R^{12}$ are each methyl.
In some embodiments, $R^9$ and $R^{12}$ are each methyl, and $R^{10}$ and $R^{11}$ are each H.
In some embodiments, $R^9$, $R^{11}$, and $R^{12}$ are each methyl, and $R^{10}$ is H.
In some embodiments, $R^9$, $R^{10}$, and $R^{12}$ are each methyl, and $R^{11}$ is H.
In some embodiments, $R^8$ is selected from $C_{16}$ alkyl, $C_{16}$ alkenyl, $C_{16}$ haloalkyl, and $C_{16}$ haloalkenyl.
In some embodiments, $R^8$ is $C_{16}$ alkyl or $C_{16}$ alkenyl.
In some embodiments, X is selected from α-tocopheryl, β-tocopheryl, γ-tocopheryl, δ-tocopheryl, α-tocotrienyl, β-tocotrienyl, γ-tocotrienyl, and δ-tocotrienyl.
In some embodiments, $R^1$ is

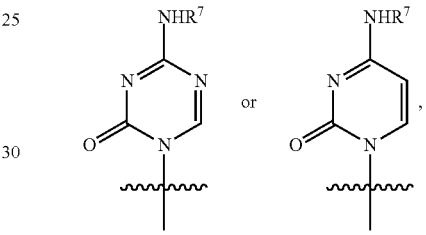

$R^2$ and $R^3$ are each independently selected from H, halo, and OH, provided that $R^2$ and $R^3$ cannot both be OH;
$R^7$ is H or methyl;
$R^{6a}$ is selected from absent, H, and $C_{1-6}$ alkyl;
W is O; and
X is selected from -tocopheryl, β-tocopheryl, γ-tocopheryl, δ-tocopheryl, α-tocotrienyl, β-tocotrienyl, γ-tocotrienyl, and δ-tocotrienyl.
In some embodiments, X is selected from α-tocopheryl, β-tocopheryl, γ-tocopheryl, δ-tocopheryl, α-tocotrienyl, β-tocotrienyl, γ-tocotrienyl, and δ-tocotrienyl.
In some embodiments, $R^1$ is

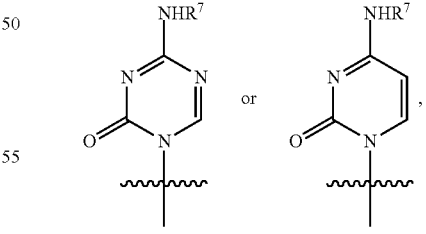

$R^2$ and $R^3$ are each independently selected from H, halo, and OH, provided that $R^2$ and $R^3$ cannot both be OH;
$R^7$ is H;
$R^{6a}$ is selected from absent, H, and $C_{1-6}$ alkyl;
W is O; and
X is selected from -tocopheryl, β-tocopheryl, γ-tocopheryl, δ-tocopheryl, α-tocotrienyl, β-tocotrienyl, γ-tocotrienyl, and δ-tocotrienyl.

In some embodiments, $R^1$ is

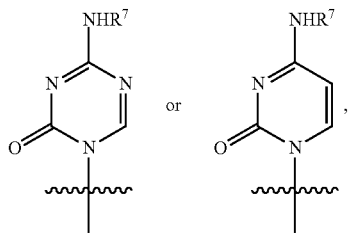

$R^2$ and $R^3$ are each independently selected from H, halo, and OH, provided that $R^2$ and $R^3$ cannot both be OH, and provided that $R^2$ and $R^3$ cannot both be H;

$R^7$ is H or methyl;

$R^{6a}$ is selected from absent, H, and $C_{1-6}$ alkyl;

W is O; and

X is selected from -tocopheryl, β-tocopheryl, γ-tocopheryl, δ-tocopheryl, α-tocotrienyl, β-tocotrienyl, γ-tocotrienyl, and δ-tocotrienyl.

In some embodiments, $R^1$ is

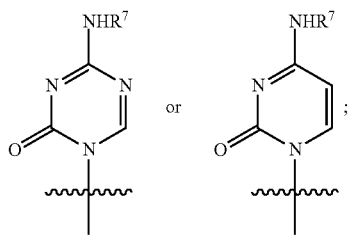

$R^2$ and $R^3$ are each independently selected from H, halo, and OH, provided that $R^2$ and $R^3$ cannot both be OH;

$R^7$ is H or methyl;

$R^{6a}$ is selected from absent, H, and $C_{1-6}$ alkyl;

W is O; and

X is selected from

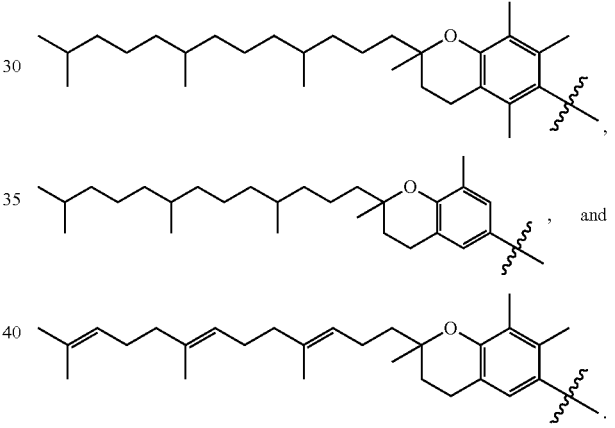

In some embodiments, $R^1$ is

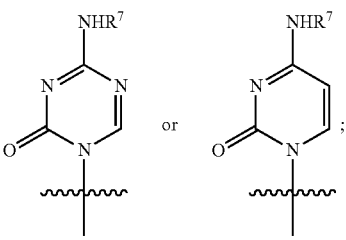

$R^2$ and $R^3$ are each independently selected from H, halo, and OH, provided that $R^2$ and $R^3$ cannot both be OH, and provided that $R^2$ and $R^3$ cannot both be H;

$R^7$ is H or methyl;

$R^{6a}$ is selected from absent, H, and $C_{1-6}$ alkyl;

W is O; and

X is selected from

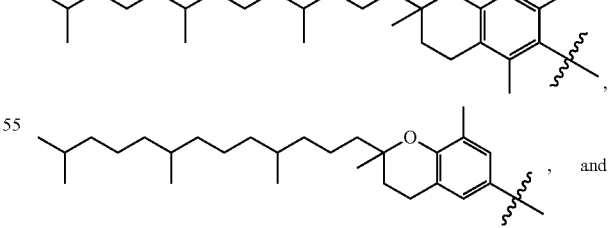

In some embodiments, W is O and X is selected from

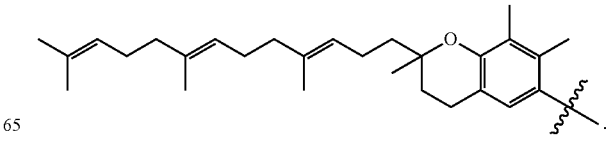

In some embodiments, the compound is selected from:
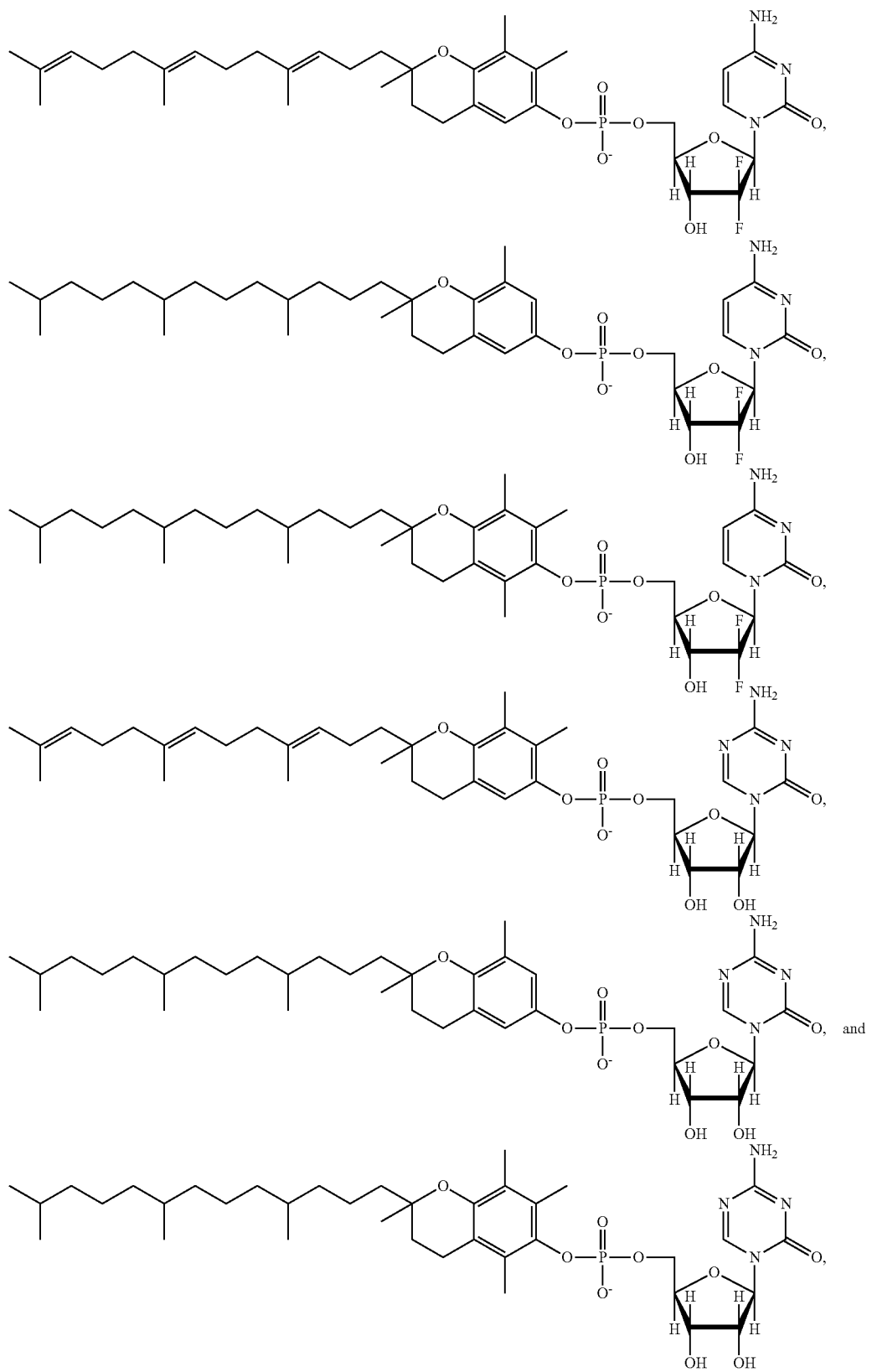
or a pharmaceutically acceptable salt thereof.

Definitions

At various places in the present specification, substituents of compounds of the disclosure are disclosed in groups or in ranges. It is specifically intended that the disclosure include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

It is further intended that the compounds of the disclosure are stable. As used herein "stable" refers to a compound that is sufficiently robust to survive isolation to a useful degree of purity from a reaction mixture.

It is further appreciated that certain features of the disclosure, which are, for clarity, described in the context of separate embodiments, can also be provided in combination in a single embodiment. Conversely, various features of the disclosure which are, for brevity, described in the context of a single embodiment, can also be provided separately or in any suitable subcombination.

"Optionally substituted" groups can refer to, for example, functional groups that may be substituted or unsubstituted by additional functional groups. For example, when a group is unsubstituted, it can be referred to as the group name, for example alkyl or aryl. When a group is substituted with additional functional groups, it may more generically be referred to as substituted alkyl or substituted aryl.

As used herein, the term "alkyl" is meant to refer to a saturated hydrocarbon group which is straight-chained (e.g., linear) or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 30, from 1 to about 24, from 2 to about 24, from 1 to about 20, from 2 to about 20, from 1 to about 10, from 1 to about 8, from 1 to about 6, from 1 to about 4, or from 1 to about 3 carbon atoms.

As used herein, the term "alkylene" refers to a linking alkyl group.

As used herein, "alkenyl" refers to an alkyl group having one or more double carbon-carbon bonds. The alkenyl group can be linear or branched. Example alkenyl groups include ethenyl, propenyl, and the like. An alkenyl group can contain from 2 to about 30, from 2 to about 24, from 2 to about 20, from 2 to about 10, from 2 to about 8, from 2 to about 6, or from 2 to about 4 carbon atoms.

As used herein, "alkenylene" refers to a linking alkenyl group.

As used herein, "haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like.

As used herein, "haloalkylene" refers to a linking haloalkyl group.

As used herein, "haloalkenyl" refers to an alkenyl group having one or more halogen substituents.

As used herein, "haloalkenylene" refers to a linking haloalkenyl group.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms.

As used herein, "arylene" refers to a linking aryl group.

As used herein, a "heteroaryl" refers to an aromatic heterocycle having at least one heteroatom ring member such as sulfur, oxygen, or nitrogen. Heteroaryl groups include monocyclic and polycyclic (e.g., having 2, 3 or 4 fused rings) systems. Any ring-forming N atom in a heteroaryl group can also be oxidized to form an N-oxo moiety. Examples of heteroaryl groups include without limitation, pyridyl, N-oxopyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, "heteroarylene" refers to a linking heteroaryl group.

As used herein, "acyl" refers to any group or organic radical such as H, alkyl, or alkenyl (the alkyl or alkenyl can be further substituted with an alkyl, alkoxy, cycloalkylamino, hydroxy, or halo) attached to a carbonyl (C=O) moiety. The acyl group is attached to the parent structure through the carbonyl moiety.

As used herein, the term "phosphate ester" refers to the (O)PO$_3$ central portion of an organophosphate having up to three side chains. The side chains can be, for example, a nucleoside (or nucleoside analogue) side chain, a vitamin E side chain and H or an alkyl. For example, an organophosphate can have a general formula of

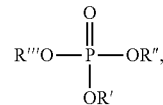

where R" is a vitamin E side chain, and R'" is a nucleoside or nucleoside analogue side chain. In some embodiments, when R' is H, at pH 7 or above, the phosphate ester can be deprotonated, such that the organophosphate has a general formula of

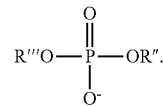

As used herein, the term "phosphoramidate" linker refers to the (O)PO$_2$N central portion of an organophosphoramidate. The phosphoramidate can have a nucleoside (or nucleoside analogue) side chain, a vitamin E side chain, and H or alkyl side chains. For example, a organophosphoramidate can have a general formula of

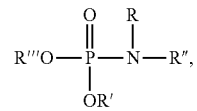

where R" is a vitamin E side chain, and R'" is a nucleoside or nucleoside analogue side chain. In some embodiments, when R' is H, at pH 7 or above, the organophosphoramidate can be deprotonated, such that the organophosphate has a general formula of

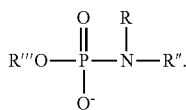

As used herein, "heteroalkyl" refers to an alkyl group having at least one heteroatom such as sulfur, oxygen, or nitrogen.

As used herein, "heteroalkylene" refers to a linking heteroalkyl group.

As used herein, "halo" or "halogen" includes fluoro, chloro, bromo, and iodo.

As used herein, "alkoxy" refers to an —O-alkyl group. Example alkoxy groups include methoxy, ethoxy, propoxy (e.g., n-propoxy and isopropoxy), t-butoxy, and the like.

As used herein, "haloalkoxy" refers to an —O-(haloalkyl) group.

As used herein, "amino" refers to $NH_2$.

As used herein, "alkylamino" refers to an amino group substituted by an alkyl group.

As used herein, "dialkylamino" refers to an amino group substituted by two alkyl groups.

The compounds described herein can be asymmetric (e.g., having one or more stereocenters). All stereoisomers, such as enantiomers and diastereomers, are intended unless otherwise indicated.

Compounds of the present disclosure that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms.

Compounds of the disclosure also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, amide—imidic acid pairs, enamine—imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the disclosure can also include all isotopes of atoms occurring in the intermediates or final compounds. Isotopes include those atoms having the same atomic number but different mass numbers. For example, isotopes of hydrogen include tritium and deuterium. Such compounds are useful, for example, as analytical tools or probes in biological assays. In some embodiments, replacement of hydrogen by deuterium or tritium, or the replacement of a carbon by a $^{13}C$- or $^{14}C$-enriched carbon can serve to improve the absorption, distribution, metabolism and excretion (ADME) profile; safety; tolerability; and therapeutic efficacy of the isotopically-enriched compound relative to the corresponding non-isotopically-enriched compound.

In some embodiments, the compounds of the disclosure, and salts thereof, are substantially isolated. By "substantially isolated" is meant that the compound is at least partially or substantially separated from the environment in which it was formed or detected. Partial separation can include, for example, a composition enriched in the compound of the disclosure. Substantial separation can include compositions containing at least about 50%, at least about 60%, at least about 70%, at least about 80%, at least about 90%, at least about 95%, at least about 97%, or at least about 99% by weight of the compound of the disclosure, or salt thereof. Methods for isolating compounds and their salts are routine in the art.

Unless otherwise defined, all technical and scientific terms used herein have the same meaning as commonly understood by one of ordinary skill in the art. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Nucleoside or Nucleoside Analogue

As discussed above, the compounds of the present disclosure include a nucleoside or a nucleoside analogue. "Nucleosides" refer to molecules including a heterocyclic nucleobase, such as cytosine, aza-cytosine, uracil, thymine, adenine, or guanine, linked to a sugar unit (e.g., ribose or deoxyribose). In nucleoside analogues, either the nucleobase or the sugar unit has been modified. For example, modifications to the nucleobase can include azotation, halogenation, or N-conjugation, while modifications to the sugar can include halogenation, methylation, ring opening, saturation, hydroxylation, or dehydroxylation. The nucleoside analogues include nucleosides that have been modified for medicinal purposes. For example, nucleoside analogues can include cytarabine, fludarabine, cladribine, gemcitabine, clofarabine, nelaribine, capecitabine, floxuridine, deoxycoformyxin, pentostatin, edoxudine, vidarabine, ribavirin, brivudine, idoxudine, trifluridine, acyclovir, zidovudine, ganciclovir, didanosine, zalcitabine, stavudine, lamivudine, emtricitabine, entecavir, telbivudine, and clevudine.

The nucleoside or nucleoside analogue can have a suitable functional group, or that can be modified to include a suitable functional group, that can be covalently coupled to a vitamin E derivative via a linker to provide a compound of the disclosure. Representative functional groups include, for example, hydroxyl groups (—OH).

In one embodiment, the compound of the present disclosure is derived from a nucleoside or a nucleoside analogue that is substantially insoluble in water. In another embodiment, the compound is derived from a nucleoside or a nucleoside analogue that is substantially insoluble in organic solvents. In another embodiment, the compound is derived from a nucleoside or nucleoside analogue that is substantially insoluble in water and substantially insoluble in organic solvents. In one embodiment, the compound has a solubility in water at room temperature less than about 1000 μg/mL. In one embodiment, the compound has a solubility in water at room temperature less than about 500 µg/mL. In one embodiment, the compound has a solubility in water at room temperature less than about 100 µg/mL. In one embodiment, the compound has a solubility in water at room temperature less than about 25 µg/mL.

Vitamin E

As discussed above, the nucleosides or nucleoside analogues can be conjugated to a vitamin E derivative. There are two main forms of vitamin E, tocopherols and tocotrienols.

The terms "tocopherol moiety" and "tocotrienol moiety" refer to a chemical moiety that is derived from a family of natural or synthetic compounds, also known by their generic names, tocol or vitamin E. These compounds include a chroman head having a phenolic alcohol at the 6-position (C-6) and a phytyl tail at the 2-position (C-2). In some embodiments, the tocopherol or tocotrienol moiety has an amine (e.g., a primary amine, a secondary amine) instead of a hydroxyl at the 6-position (C-6) and a phytyl tail at the 2-position (C-2).

Tocopherols constitute a series of related benzopyranols (or methyl tocols) in which the C-2 phytyl (sixteen carbon) side chain is saturated. Representative tocopherols include α-tocopherol, (d-form, dl-form, l-form), β-tocopherol (d-form, dl-form, l-form), γ-tocopherol (d-form, dl-form, l-form), and δ-tocopherol (d-from, dl-form, l-form). Among tocopherols, α-tocopherol is the most abundant. Tocotrienols are similar in structure to tocopherols except that the trienols have three double bonds in the C-2 phytyl side chain.

Tocopherol and tocotrienol compounds useful in making the compounds of the disclosure include those shown below.

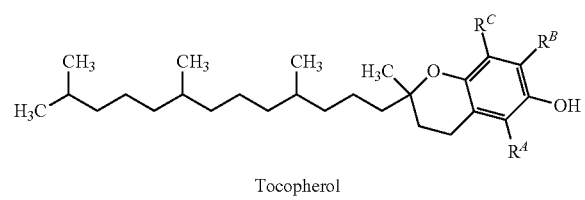

Tocopherol

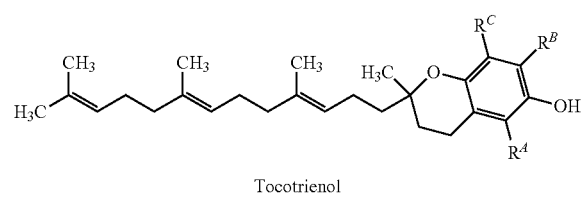

Tocotrienol

| Compound | $R^A$ | $R^B$ | $R^C$ |
|---|---|---|---|
| alpha (α) | $CH_3$ | $CH_3$ | $CH_3$ |
| beta (β) | $CH_3$ | H | $CH_3$ |
| gamma (γ) | H | $CH_3$ | $CH_3$ |
| delta (δ) | H | H | $CH_3$ |

While tocopherol or tocotrienol moieties having hydroxyl at the 6-position have been described above, in some embodiments, the tocopherol or tocotrienol (α, β, γ, and δ) moiety has an amine (e.g., a primary amine, a secondary amine) instead of a hydroxyl at the 6-position (C-6) and a phytyl tail at the 2-position (C-2).

As an example, tocopherol and tocotrienol conjugates of some drugs, such as paclitaxel, camptothecin, docetaxel, doxorubicin, hydroxyzine, have been described, for example, in U.S. Pat. No. 7,223,770, the disclosure of which is incorporated herein in its entirety. However, in contrast to the present disclosure, U.S. Pat. No. 7,223,770 focuses on formulations, rather than nucleoside or nucleoside analogue conjugates for intracellular delivery of monophosphorylated nucleosides or nucleoside analogues.

Synthesis

In another aspect, methods for making the compounds of the disclosure are provided. There are many ways to covalently couple a vitamin E to a nucleoside or nucleoside analogue to form a compound of the disclosure. For example, a tocopherol or tocotrienol may be functionalized at the hydroxyl group with a reagent such as phosphorus oxychloride. The resulting acid chloride can then be reacted with an appropriately functionalized nucleoside or nucleoside analogue to provide a tocopherol or tocotrienol-modified compound. Examples of synthesis of vitamin E-modified compounds of the disclosure are shown in Schemes 1 and 2.

Scheme 1. Synthesis of vitamin E-modified nucleoside or nucleoside analogue.

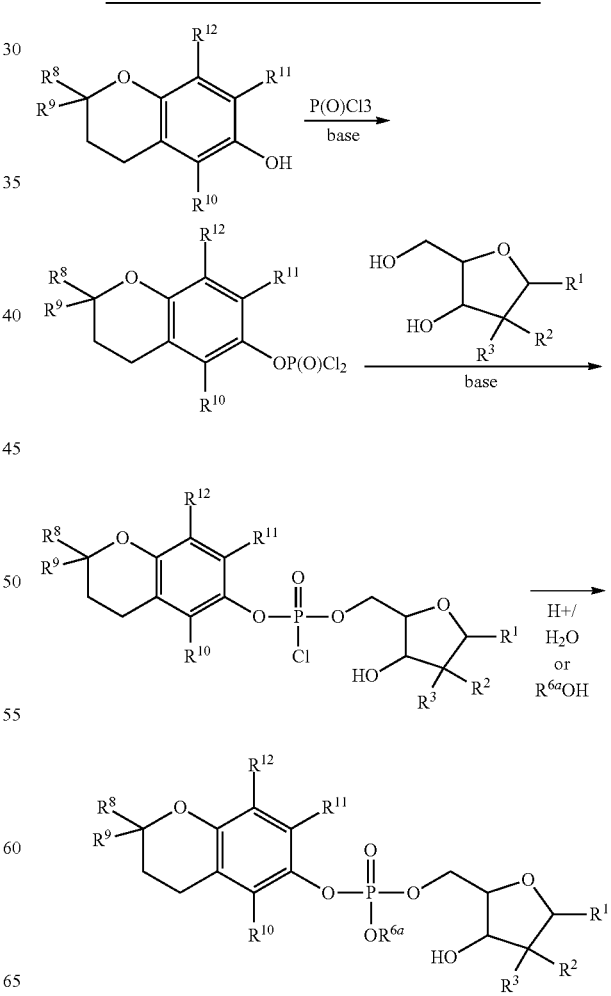

Scheme 2. Synthesis of vitamin E-modified nucleoside or nucleoside analogue.

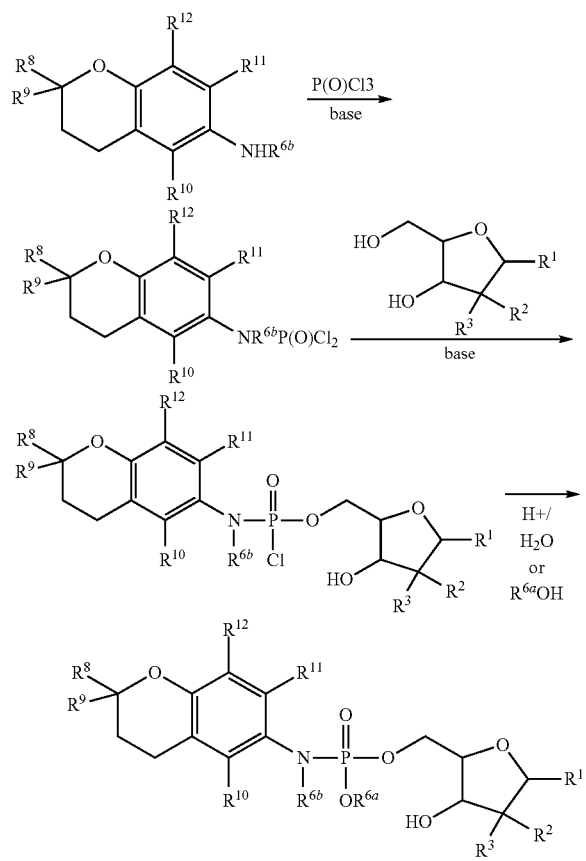

Compositions

In another aspect, the present disclosure provides compositions that include the compounds of the disclosure. The compositions include one or more compounds of the disclosure, optionally one or more additional therapeutic agents, and a medium (e.g., a lipophilic medium). In one embodiment, a vitamin E-modified nucleoside or nucleoside analogue is dissolved in the lipophilic medium. Because of the vitamin E derivative, the compound has improved lipophilicity compared to the unmodified nucleoside or nucleoside analogue. The lipophilic medium (or carrier) of the composition can be any one of a variety of lipophilic mediums including, for example, oils. In one embodiment, the lipophilic medium includes a vitamin E (e.g., α-tocopherol). Representative oils useful as the lipophilic medium include the following:

Fatty acids and esters thereof, including carboxylic acids of various chain lengths, mostly straight chain, but which could be branched, examples of which include capric, caprylic, caproic, lauric, myristic, stearic, oleic, linoleic, behenic, and as well as saturated or unsaturated fatty acids and esters;

Fatty acids esterified with glycerin to form mono-, di-, or triglycerides, which can be synthetic or derived from natural sources, including, but not limited to, for example, glycerides such as soybean oil, cottonseed oil, rapeseed oil, fish oil, castor oil, Capmul MCM, Captex 300, Miglyol 812, glyceryl monooleate, triacetin, acetylated monoglyceride, tristearin, glyceryl behenate, and diacetyl tartaric acid esters of monoglycerides;

Glycerides conjugated to other moieties, such as polyethylene glycol (for example, Labrasol, Labrafac, Cremophor EL);

Phospholipids, either natural or synthetic, such as dimyristyl phosphatidylcholine, egg lecithin, and pegylated phospholipids;

Other fatty esters including fatty alcohols (myristyl myristate, isopropyl palmitate), or sugars (sorbitan monooleate, SPAN 80, Tween 80, sucrose laurate);

Fatty alcohols such as stearyl alcohol, lauryl alcohol, benzyl alcohol, or esters or ethers thereof, such as benzyl benzoate;

Fat-soluble vitamins and derivatives, for example, vitamin E (including all of the tocopherols and tocotrienols, and tocopherol and tocotrienol derivatives, such as vitamin E succinate, vitamin E acetate, and vitamin E succinate polyethylene glycol (TPGS)).

Organic co-solvents can also be used in the compositions, optionally in combination with water, including for example, ethanol, polyethylene glycol, propylene glycol, glycerol, N-methyl pyrrolidone, and dimethyl sulfoxide.

Compositions and Methods of Use

In a further aspect, the disclosure provides emulsion, microemulsion, and micelle formulations that include a compound of the disclosure. Methods for making the emulsion, microemulsion, and micelle formulations are also provided.

As used herein, the term "emulsion" refers to a colloidal dispersion of two immiscible liquids, such as an oil and water, in the form of droplets, whose diameter, in general, are between 0.1 and 3.0 microns and which is typically optically opaque, unless the dispersed and continuous phases are refractive index matched. Such systems possess a finite stability, generally defined by the application or relevant reference system, which may be enhanced by the addition of amphiphilic molecules or viscosity enhancers.

The term "microemulsion" refers to a thermodynamically stable isotropically clear dispersion of two immiscible liquids, such as an oil and water, stabilized by an interfacial film of surfactant molecules. The microemulsion has a mean droplet diameter of less than 200 nm, in general between 10-50 nm. In the absence of water, mixtures of oil(s) and non-ionic surfactant(s) form clear and isotropic solutions that are known as self-emulsifying drug delivery systems (SEDDS) and can be used to improve lipophilic drug dissolution and oral absorption.

The emulsion and microemulsion formulations include an oil phase and an aqueous phase. The emulsion or microemulsion can be an oil-in-water emulsion or a water-in-oil emulsion. The oil phase includes one or more compounds of the disclosure and a lipophilic medium, as described above. In one embodiment, the compound is present in the formulation in an amount from about 0.005 to about 3.0 weight percent based on the total weight of the formulation. In one embodiment, the compound is present in the formulation in an amount from about 0.01 to about 2.5 weight percent based on the total weight of the formulation. In one embodiment, the compound is present in the formulation in an amount from about 0.1 to about 1.5 weight percent based on the total weight of the formulation. In one embodiment, the lipophilic medium is present in the formulation in an amount from about 2 to about 20 weight percent based on the total weight of the formulation. In one embodiment, the lipophilic medium is present in the formulation in an amount from about 4 to about 12 weight percent based on the total weight of the formulation. In one embodiment, the lipophilic medium is present in the formulation in an amount from about 6 to about 10 weight percent based on the total weight of the formulation.

In one embodiment of the emulsion or microemulsion, the compound is a vitamin E-modified nucleoside or nucleoside analogue, the lipophilic medium includes a vitamin E, and the aqueous medium is water.

In addition to the compounds of the disclosure, the emulsion or microemulsion formulations can include other components commonly used in emulsions and microemulsions, and particularly used in pharmaceutical emulsions and microemulsions. These components include surfactants and co-solvents, among others. Representative surfactants include nonionic surfactants such as surface active vitamin E derivatives and surface active polymers.

Suitable surface active vitamin E derivatives include vitamin E polyethylene glycol derivatives, such as vitamin E succinate polyethylene glycol (e.g., d-α-tocopherol polyethylene glycol 1000 succinate, TPGS), which is a vitamin E derivative in which a polyethylene glycol is attached by a succinic acid ester at the ring hydroxyl of vitamin E. As used herein, "vitamin E succinate polyethylene glycol" includes vitamin E succinate polyethylene glycol and derivatives of vitamin E polyethylene glycol having various ester and ether links. TPGS is a non-ionic surfactant (HLB=16-18). TPGS is reported to inhibit P-glycoprotein, a protein that contributes to the development of multi-drug resistance. Embodiments of the formulations of the disclosure that include TPGS therefore include a P-glycoprotein inhibitor. Surface active vitamin E derivatives (e.g., TPGS) can be present in the formulations of the disclosure in an amount from about 1 to about 10 weight percent, about 2 to about 6 weight percent, or about 5 weight percent, based on the total weight of the formulation.

Suitable nonionic surfactants include block copolymers of ethylene oxide and propylene oxide known as POLOXAMERS or PLUROINICS®. These synthetic block copolymers of having the general structure: $H(OCH_2CH_2)_a (OC_3H_6CH_2)_b (OCH_2CH_2)_aOH$. The following variants based on the values of a and b are commercially available from BASF Performance Chemicals (Parsippany, N.J.) under the trade name PLURONIC® and consist of the group of surfactants designated by the CTFA name of POLOXAMER 108, 188, 217, 237, 238, 288, 338, 407, 101, 105, 122, 123, 124, 181, 182, 183, 184, 212, 231, 282, 331, 401, 402, 185, 215, 234, 235, 284, 333, 334, 335, and 403. For the most commonly used POLOXAMERS 124, 188, 237, 338, and 407 the values of a and b are 12/20, 79/28, 64/37, 141/44 and 101/56, respectively. In one embodiment the nonionic surfactant is present in the formulation in an amount from about 0.5 to about 5 weight percent based on the total weight of the formulation.

Co-solvents useful in the formulations include ethanol, polyethylene glycol, propylene glycol, glycerol, N-methylpyrrolidone, dimethylamide, and dimethylsulfoxide, among others. Polyethylene glycol (PEG) is a hydrophilic, polymerized form of ethylene glycol, consisting of repeating units having the chemical structure: ($-CH_2CH_2O-$). The general formula for polyethylene glycol is $H(OCH_2CH_2)_nOH$. The molecular weight ranges from 200 to 10,000. Such various forms are described by their molecular weights, for example, PEG-200, PEG-300, PEG-400, and the like.

In a further aspect, the disclosure provides micelle formulations that include a compound of the disclosure and an aqueous phase. Micelles are organized aggregates of one or more surfactants in solution. In one embodiment, the compound is present in the formulation in an amount from about 0.005 to about 3.0 weight percent based on the total weight of the formulation. In one embodiment, the compound is present in the formulation in an amount from about 0.01 to about 2.5 weight percent based on the total weight of the formulation. In one embodiment, the compound is present in the formulation in an amount from about 0.1 to about 1.0 weight percent based on the total weight of the formulation. Suitable surfactants include those noted above, and in the amounts noted above. In one embodiment of the micelle formulation, the compound is a vitamin E-modified nucleoside or nucleoside analogue and the surfactant is vitamin E polyethylene glycol succinate (TPGS).

The micelle formulation can also include additional components such as co-solvents including those noted above. In one embodiment, the micelle formulation includes a polyethylene glycol and a lower alkyl alcohol (e.g., ethanol). In one embodiment, the co-solvents are present in an amount from about 2 to about 20 weight percent based on the total weight of the formulation. The micelle, emulsion, and microemulsion formulations include an aqueous phase. In one embodiment, the aqueous phase includes deionized water. In another embodiment, the aqueous phase includes saline. In another embodiment, the aqueous phase is saline buffered with an organic acid (e.g., succinate, citrate).

The disclosure also provides the use of the compounds of the disclosure in the manufacture of a medicament, for example, for the treatment of cell proliferative disease.

In other aspects, methods for administering a compound of the disclosure to a subject in need thereof, and methods for treating a condition treatable by administration of a therapeutically effective amount of a compound of the disclosure are also provided. These methods include the administration of the compounds, compositions, emulsion formulations, microemulsion formulations, and micelle formulations described herein.

In one embodiment, the disclosure provides a method for treating a condition that is treatable by the parent, unmodified nucleoside or nucleoside analogue (e.g., a cell proliferative disease such as cancer). In the method, a therapeutically effective amount of a compound of the disclosure is administered to a subject in need thereof.

In one embodiment, the disclosure provides a method for intracellular delivery of a monophosphorylated nucleoside or nucleoside analogue. In the method, a compound of the disclosure is contacted with a cell. When internalized into a cell, the compound is cleaved by cellular enzymes (e.g., phosphatase and/or phosphodiesterase) into the corresponding nucleoside or nucleoside analogue phosphate, and tocopherol or tocotrienol.

In one embodiment, the disclosure provides a method for treating a cell proliferative disease by administering a compound of the disclosure having a nucleoside or nucleoside analogue derived from a therapeutic drug effective in treating cell proliferative disease. Representative cell proliferative diseases treatable by the compounds of the disclosure include hematologic cancers, such as leukemia, lymphoma, and myeloma; and nonhematologic cancers, such as solid tumor carcinomas (e.g., breast, ovarian, pancreatic, colon, colorectal, lung (e.g., non-small cell lung), and bladder), sarcomas, and gliomas.

Therapeutically effective amounts of the compounds will generally range up to the maximally tolerated dosage, but the concentrations are not critical and may vary widely. The precise amounts employed by the attending physician will vary, of course, depending on the compound, route of administration, physical condition of the patient and other factors. The daily dosage may be administered as a single dosage or may be divided into multiple doses for administration.

The amount of the compound actually administered will be a therapeutically effective amount, which term is used herein to denote the amount needed to produce a substantial beneficial effect. Effective doses may be extrapolated from dose-response curves derived from in vitro or animal model test systems. The animal model is also typically used to determine a desirable dosage range and route of administration. Such information can then be used to determine useful doses and routes for administration in humans or other mammals. The determination of an effective dose is well within the capability of those skilled in the art. Thus, the amount actually administered will be dependent upon the individual to which treatment is to be applied, and will preferably be an optimized amount such that the desired effect is achieved without significant side-effects.

Therapeutic efficacy and possible toxicity of the compounds of the disclosure can be determined by standard pharmaceutical procedures, in cell cultures or experimental animals (e.g., ED50, the dose therapeutically effective in 50% of the population; and LD50, the dose lethal to 50% of the population). The dose ratio between therapeutic and toxic effects is the therapeutic index, and it can be expressed as the ratio LD50 to ED50. Modified therapeutic drug compounds that exhibit large therapeutic indices are particularly suitable in the practice of the methods of the disclosure. The data obtained from cell culture assays and animal studies may be used in formulating a range of dosage for use in humans or other mammals. The dosage of such compounds lies preferably within a range of circulating concentrations that include the ED50 with little or no toxicity. The dosage typically varies within this range depending upon the dosage form employed, sensitivity of the patient, and the route of administration. Thus, optimal amounts will vary with the method of administration, and will generally be in accordance with the amounts of conventional medicaments administered in the same or a similar form.

The compounds of the disclosure can be administered alone, or in combination with one or more additional therapeutic agents. For example, in the treatment of cancer, the compounds can be administered in combination with compounds of the present disclosure including, but not limited to, androgen inhibitors, such as flutamide and luprolide; antiestrogens, such as tomoxifen; antimetabolites and cytotoxic agents, such as daunorubicin, fluorouracil, floxuridine, interferon alpha, methotrexate, plicamycin, mecaptopurine, thioguanine, adriamycin, carmustine, lomustine, cytarabine, cyclophosphamide, doxorubicin, estramustine, altretamine, hydroxyurea, ifosfamide, procarbazine, mutamycin, busulfan, mitoxantrone, carboplatin, cisplatin, streptozocin, bleomycin, dactinomycin, and idamycin; hormones, such as medroxyprogesterone, estramustine, ethinyl estradiol, estradiol, leuprolide, megestrol, octreotide, diethylstilbestrol, chlorotrianisene, etoposide, podophyllotoxin, and goserelin; nitrogen mustard derivatives, such as melphalan, chlorambucil, methlorethamine, and thiotepa, steroids, such as betamethasone; and other antineoplastic agents, such as live *Mycobacterium bovis*, dicarbazine, asparaginase, leucovorin, mitotane, vincristine, vinblastine, and taxotere. Appropriate amounts in each case will vary with the particular agent, and will be either readily known to those skilled in the art or readily determinable by routine experimentation.

Administration of the compounds of the disclosure is accomplished by any effective route, for example, parenteral, topical, or oral routes. Methods of administration include inhalational, buccal, intramedullary, intravenous, intranasal, intrarectal, intraocular, intraabdominal, intraarterial, intraarticular, intracapsular, intracervical, intracranial, intraductal, intradural, intralesional, intramuscular, intralumbar, intramural, intraocular, intraoperative, intraparietal, intraperitoneal, intrapleural, intrapulmonary, intraspinal, intrathoracic, intratracheal, intratympanic, intrauterine, intravascular, and intraventricular administration, and other conventional means. The compounds of the disclosure having anti-tumor activity can be injected directly into a tumor, into the vicinity of a tumor, or into a blood vessel that supplies blood to the tumor.

The emulsion, microemulsion, and micelle formulations of the disclosure can be nebulized using suitable aerosol propellants that are known in the art for pulmonary delivery of the compounds.

The compounds of the disclosure may be formulated into a composition that additionally comprises suitable pharmaceutically acceptable carriers, including excipients and other compounds that facilitate administration of the compound to a subject. Further details on techniques for formulation and administration may be found in the latest edition of "Remington's Pharmaceutical Sciences" (Maack Publishing Co., Easton, Pa.).

Compositions for oral administration may be formulated using pharmaceutically acceptable carriers well known in the art, in dosages suitable for oral administration. Such carriers enable the compositions containing the compounds of the disclosure to be formulated as tablets, pills, dragees, capsules, liquids, gels, syrups, slurries, suspensions, suitable for ingestion by a subject. Compositions for oral use may be formulated, for example, in combination with a solid excipient, optionally grinding the resulting mixture, and processing the mixture of granules, after adding suitable additional compounds, if desired, to obtain tablets or dragee cores. Suitable excipients include carbohydrate or protein fillers. These include, but are not limited to, sugars, including lactose, sucrose, mannitol, or sorbitol, starch from corn, wheat, rice, potato, or other plants; cellulose such as methyl cellulose, hydroxypropylmethyl-cellulose, or sodium carboxymethylcellulose; and gums including arabic and tragacanth; as well as proteins, such as gelatin and collagen. If desired, disintegrating or solubilizing agents may be added, such as the crosslinked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage).

Compounds for oral administration may be formulated, for example, as push-fit capsules made of gelatin, as well as soft, sealed capsules made of gelatin and a coating such as glycerol or sorbitol. Push-fit capsules may contain the compounds mixed with filler or binders such as lactose or starches, lubricants such as talc or magnesium stearate, and, optionally, stabilizers. In soft capsules, the covalent conjugates may be dissolved or suspended in suitable liquids, such as fatty oils, liquid paraffin, or liquid polyethylene glycol with or without stabilizers.

For topical or nasal administration, penetrants appropriate to the particular barrier to be permeated are typically used in the formulation. Examples of these are 2-pyrrolidone, N-methyl-2-pyrrolidone, dimethylacetamide, dimethyl-formamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface-active agents. Keratolytic agents such as those known in the art may also be included. Examples are salicylic acid and sulfur. For topical administration, the composition may be in the form of a transdermal ointment or patch for systemic delivery of the compound and may be prepared in a conventional manner (see, e.g., Barry, Dermatological Formulations (Drugs and the Pharmaceutical Sciences—Dekker); Harry's Cosmeticology (Leonard Hill Books).

For rectal administration, the compositions may be administered in the form of suppositories or retention enemas. Such compositions may be prepared by mixing the compounds with a suitable non-irritating excipient that is solid at ordinary temperatures but liquid at the rectal temperature and will therefore melt in the rectum to release the drug. Suitable excipients include, but are not limited to, cocoa butter and polyethylene glycols.

The amounts of each of these various types of additives will be readily apparent to those skilled in the art, optimal amounts being the same as in other, known formulations designed for the same type of administration.

Compositions containing the compounds of the disclosure may be manufactured in a manner similar to that known in the art (e.g., by means of conventional mixing, dissolving, granulating, dragee-making, levigating, emulsifying, encapsulating, entrapping or lyophilizing processes). The compositions may also be modified to provide appropriate release characteristics, sustained release, or targeted release, by conventional means (e.g., coating). As noted above, in one embodiment, the compounds are formulated as an emulsion.

Compositions containing the compounds may be provided as a salt and can be formed with many acids, including but not limited to hydrochloric, sulfuric, acetic, lactic, tartaric, malic, and succinic. Salts tend to be more soluble in aqueous or other protonic solvents than are the corresponding free base forms.

After compositions formulated to contain a compound and an acceptable carrier have been prepared, they can be placed in an appropriate container and labeled for use. Thus, in another aspect, the disclosure provides kits.

Vitamin E-modified nucleosides or nucleoside analogues of the disclosure are suitable for administration as oil-in-water emulsions and micelle formulations. The compounds provide for high drug loading to enable small volumes for administration.

Emulsions containing the vitamin E-modified nucleosides or nucleoside analogues of the disclosure provide for enhanced stability and enhanced activity of the nucleosides or nucleoside analogues. Vitamin E-modified compounds can achieve high permeation through lipoidal membranes of tumor cells. Greater anti-tumor response without an increase in toxicity may be provided by the vitamin E-modified compounds of the disclosure as compared to unmodified nucleoside and nucleoside analogues and currently available nucleoside and nucleoside analogues.

The following example is provided to illustrate, not limit, the invention.

EXAMPLE

Example 1. Synthesis and In Vitro Evaluation of Vitamin E-Modified Gemcitabines

Gemcitabine prodrugs of Table 1 were synthesized and were evaluated against a variety of cancer cells.

TABLE 1

Gemcitabine prodrugs.

| Name | Structure |
|---|---|
| D-α-tocopheryl phosphate-5'-gemcitabine, triethylammonium salt (Compound 1) | 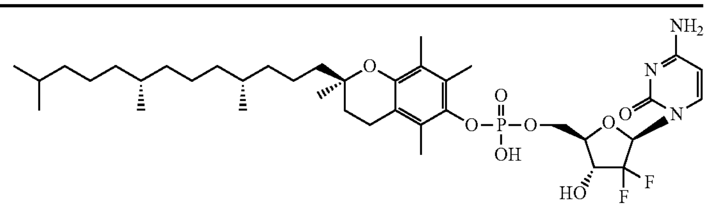 |
| D-δ-tocopheryl phosphate-5'-gemcitabine, triethylammonium salt (Compound 2) | 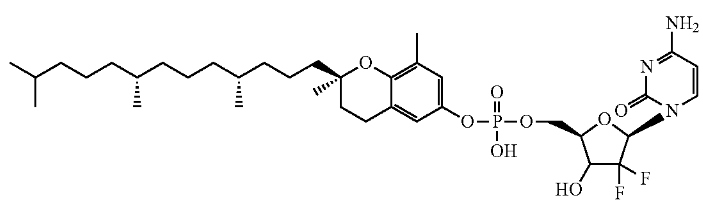 [SMILES: Cc1cc(OP(=O)(O)OC[C@H]2O[C@@H](n3ccc(N)nc3=O)C(F)(F)C2O)cc2c1O[C@](C)(CCC[C@H](C)CCC[C@H](C)CCCC(C)C)CC2] |
| D-γ-tocotrienyl phosphate-5'-gemcitabine, triethylammonium salt (Compound 3) | 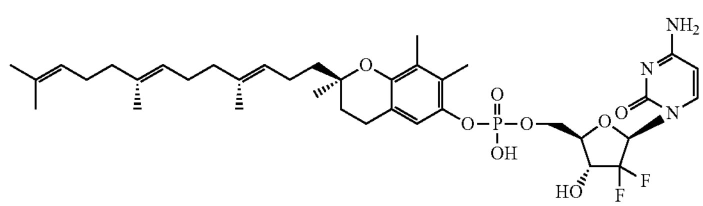 |

Table 2 demonstrates that activity of gemcitabine in vitro was well preserved, particularly in the case of breast cancer, with the tocopherol/tocotrienol gemcitabine prodrugs. It is believed that 5-aza nucleosides (e.g., 5-azacytidine) will also derive benefit from a 5'-prodrug construct because the vitamin E conjugate would be more stable to hydrolysis. The conjugate of α-tocopheryl phosphate (Compound 1) was less active than the conjugate of δ-tocopheryl phosphate (Compound 2). This may be due to the steric hindrance of the three methyl groups in proximity to the phosphate in the case of Compound 1, which render enzymatic cleavage more difficult. The results suggest that δ-tocotrienylphosphate may be a suitable carrier, because δ-tocotrienylphosphate has a single more distant methyl group, rather than γ-tocotrienyl phosphate, which has two methyl groups. Furthermore, δ-tocotrienol appeared to be at least as active in its antiproliferative activity, when compared to γ-tocotrienol.

TABLE 2

Comparison of in vitro cytotoxicity between gemcitabine, Compound 1, Compound 2, and Compound 3.

|  | Breast MDA-MB-231 | Non-Small Cell Lung NCI-H460 | Colon HCT-116 |
| --- | --- | --- | --- |
| Gemcitabine | 0.11 | 0.02 | 0.01 |
| α-tocopheryl phosphate | 23.40 | 52.24 | 46.86 |
| Compound 1 | 22.70 | 23.75 | 26.13 |
| δ-tocopheryl phosphate | 29.56 | 69.67 | 70.58 |
| Compound 2 | 5.08 | 1.69 | 3.67 |
| γ-tocotrienyl phosphate | 26.42 | 69.14 | 55.71 |
| Compound 3 | 4.90 | 4.75 | 4.01 |

Scheme 3 shows a proposed intracellular metabolism of tocopherol/tocotrienol phosphate nucleoside by phosphatase or phosphodiesterase to tocopherol/tocotrienol and nucleoside monophosphate. Based on the activity of known enzymes, it is believed that cleavage by phosphatases or phosphodiesterase result in production of gemcitabine monophosphate (MP) and tocopherol, tocotrienol, rather than gemcitabine and tocopherol/tocotrienol functionalized with phosphate. The intracellular metabolism is important because a rate limiting step in nucleotide synthesis is generation of the MP. For example, gemcitabine is phosphorylated to the MP by deoxycytidine kinase (dCK) and dCK "deficiency" can be responsible for acquired and intrinsic resistance. Delivery of MP-nucleosides to cells has been a challenge because phosphates are acidic and negatively charged at physiologic pH, and phosphohydrolases rapidly convert MP-nucleosides to corresponding nucleosides.

Scheme 3. Proposed intracellular metabolism of tocopherol/tocotrienol phosphate nucleoside by phosphatase or phosphodiesterase to tocopherol/tocotrienol and nucleoside monophosphate.

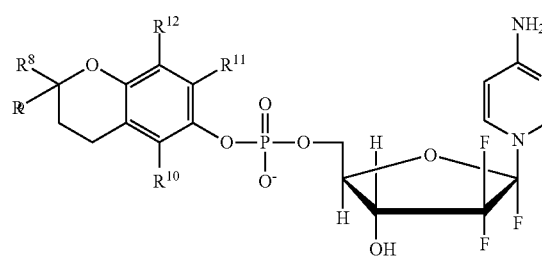
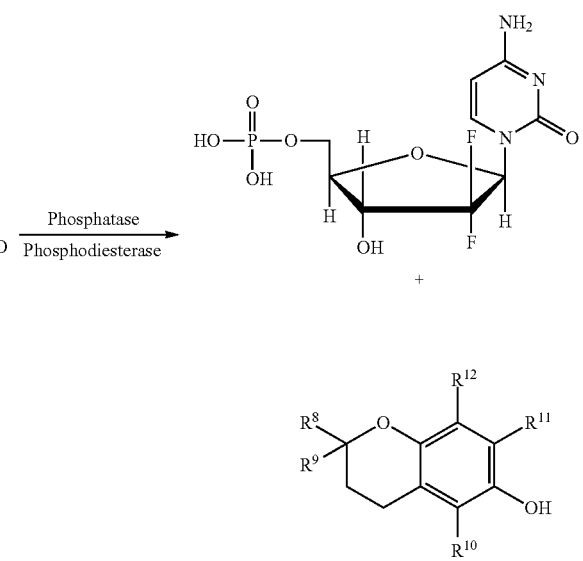

To determine whether the prodrugs were imported as intact prodrugs into the cell by a non-nucleoside transporter dependent mechanism, or dissociated outside the cell into carrier and active, cellular cytotoxicity was evaluated in the presence and absence of dipyridamole an inhibitor of nucleoside transport.

In general, growth inhibitory effects of gemcitabine and prodrugs were evaluated in breast (MDA), lung (H460) and colon (H116) cancer cell lines by seeding the cell lines in 96-wells plates and exposing the cells to various drug concentrations for 72 hr. Standard sulforhodamine B (SRB) assay was then performed. Control wells did not include dipyridamole and treated wells included a final dipyridamole concentration of 1 μM. The results are shown in Table 3.

TABLE 3

Comparison of in vitro cytotoxicity of gemcitabine with Compound 2 and Compound 3 in the presence or absence of dipyridamole.

$GI_{50}$ (μM) SRB

|  | MDA Breast | | H460 Lung | | H116 Colon | |
| --- | --- | --- | --- | --- | --- | --- |
|  |  | dipyridamole |  | dipyridamole |  | dipyridamole |
| Gemcitabine | 3.08 | 56.77 | 0.02 | 0.82 | 0.03 | 2.39 |
| Compound 2 | 17.16 | 23.30 | 2.14 | 1.47 | 3.07 | 6.74 |
| Compound 3 | 30.34 | 27.77 | 7.16 | 15.98 | 5.55 | 12.61 |

Dipyridamole increased the $GI_{50}$ of gemcitabine from 18 to 80-fold, while that of Compound 2 and Compound 3 was increased at most 2.3-fold. Thus, dipyridamole did not block the tocopherol/tocotrienol-modified drugs (Compounds 2 and 3) as it did free gemcitabine, suggesting that tocopherol/tocotrienol conjugates are not dependent on nucleoside transporters for entry into the cell and penetrate the cell as intact molecules where they dissociate as carrier and nucleoside monophosphate.

To further confirm that tocopherol/tocotrienol-modified drugs are imported as intact molecules and then dissociate intracellularly into monophosphorylated nucleoside and carrier, i.e., tocopherol/tocotrienol, Compound 2 was tested for activity against gemcitabine in wild type (WT) leukemic CEM cells and CEM cells without deoxycytidine kinase (dCK). In the absence of dCK, gemcitabine is not phosphorylated to gemcitabine monophosphate a precursor to the therapeutically active di- and triphosphates.

TABLE 4

IC50 values of gemcitabine and Compound 2.

| Cell Line | IC$_{50}$ (μM) | |
| --- | --- | --- |
|  | Gemcitabine | Compound 2 |
| CEM WT | 0.002 | 0.59 |
| CEM dCK(—) | 124.5 | 19.2 |

As shown in Table 4, gemcitabine IC$_{50}$ went from 0.002 μM in dCK WT cells to 124.5 μM in dCK (−) cells, an increase of 62,250-fold. Compound 2 IC$_{50}$ went from 0.59 μM to 19.2 μM, an increase of only 32.5-fold. Viewed another way, the IC$_{50}$ of gemcitabine was lower than Compound 2 in dCK WT cells by 295-fold, but the IC$_{50}$ of Compound 2 in dCK (−) cells was lower than gemcitabine by 6.5-fold.

These data are compatible with the intracellular delivery by Compound 2 of a monophosphorylated nucleoside.

The half-life of gemcitabine in humans for short infusions was 42 to 94 minutes. The short half-life was a result of deamination by cytidine deaminase to the inactive uracil metabolite, 2'-deoxy-2',2'-difluorouridine. As Compound 2 is likely not a substrate for cytidine deaminase, it is believed that Compound 2 can demonstrate in vivo even greater therapeutic benefit over gemcitabine.

Example 2. Aqueous Solubility Determination

Aqueous solubility (μM) was determined by comparing the peak area of the principal peak in a calibration standard (200 μM) containing organic solvent (methanol/water, 60/40, v/v) with the peak area of the corresponding peak in a buffer sample. In addition, chromatographic purity (%) was defined as the peak area of the principal peak relative to the total integrated peak area in the HPLC chromatogram of the calibration standard. A chromatogram of the calibration standard of each test compound, along with a UV/VIS spectrum with labeled absorbance maxima, was generated. By this same method Compound 2 was found to be soluble in PBS (pH 7.4) at concentrations of greater than 10 mg/ml and simulated intestinal fluid at >200 μM.

Example 3. Intrinsic Clearance Determination (Microsomes, S9, Cryopreserved Hepatocytes, Recombinant CYP, Recombinant UGT)

Metabolic stability, expressed as percent of the parent compound remaining, was calculated by comparing the peak area of the compound at the time point relative to that at time-0. The half-life (T1/2) was estimated from the slope of the initial linear range of the logarithmic curve of compound remaining (%) vs. time, assuming the first-order kinetics. The apparent intrinsic clearance (CL$_{int}$, in μL/min/pmol, μL/min/mg or μL/min/Mcell) was calculated according to the following formula:

CL$_{int}$=0.693T1/2*(mg protein/μL or million cells/μL or pmol CYP isozyme/μL)

δ-tocopherol gemcitabine was stable in the presence of human liver microsomes with an intrinsic clearance half-life of greater than 60 minutes, suggesting that it would not be subject to significant first pass metabolism.

While preferred embodiments have been described, it will be appreciated that various changes can be made therein without departing from the spirit and scope of the disclosure.

The embodiments of the invention in which an exclusive property or privilege is claimed are defined as follows:

1. A compound according to Formula (II):

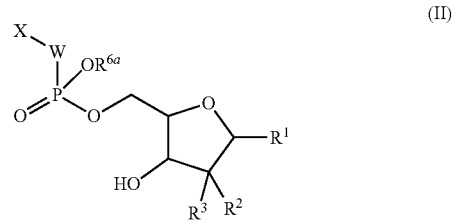

or a pharmaceutically acceptable salt thereof, wherein:
R$^1$ is selected from

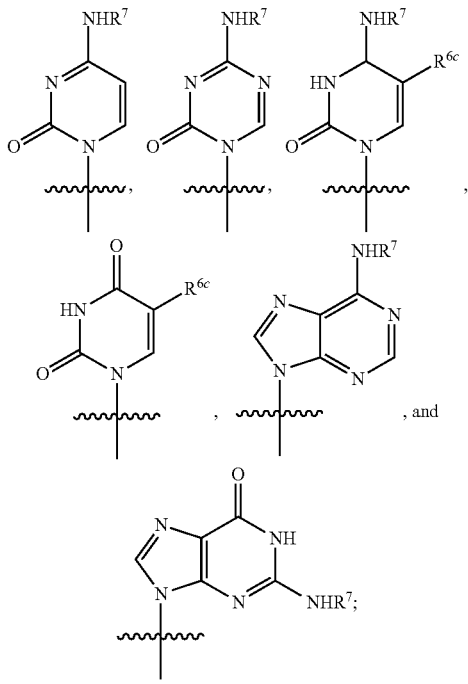

R$^2$ and R$^3$ are each independently selected from H, halo, and OH, provided that R$^2$ and R$^3$ are not both OH;
R$^{6a}$ is selected from absent, H, and C$_{1-6}$ alkyl;
W is O or NR$^{6b}$, $R^{6b}$ is selected from H, $C_{1-6}$ alkyl, $C_{1-6}$ alkoxy, wherein said $C_{1-6}$ alkyl and $C_{1-6}$ alkoxy are each optionally substituted with 1 or 2 substituents independently selected from aryl and heteroaryl, wherein said aryl or heteroaryl is optionally substituted with 1 or 2 substituents independently selected from cyano and nitro, $R^{6c}$ is selected from H, $C_{1-6}$ alkyl, and $C_{1-6}$ haloalkyl;

$R^7$ is H or $C_{1-6}$ alkyl; and

X is

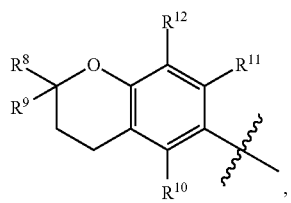

wherein $R^8$ is selected from $C_{12-24}$ alkyl, $C_{12-24}$ alkenyl, $C_{12-24}$ haloalkyl, and $C_{12-24}$ haloalkenyl, $R^9$ is selected from H, $C_{1-6}$ alkyl, and halo, $R^{10}$ is H, $R^{11}$ and $R^{12}$ are each independently selected from H, $C_{1-6}$ alkyl, and halo.

2. The compound of claim 1, or a pharmaceutically acceptable salt thereof,
wherein $R^1$ is

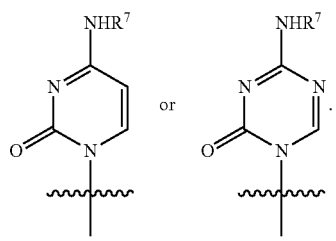

3. The compound of claim 1, or a pharmaceutically acceptable salt thereof, wherein $R^2$ and $R^3$ are each F.

4. The compound of claim 1, or a pharmaceutically acceptable salt thereof, wherein $R^{6a}$ and $R^{6b}$ are each H.

5. The compound of claim 1, or a pharmaceutically acceptable salt thereof, wherein $R^{6c}$ is methyl or trifluoromethyl.

6. The compound of claim 1, or a pharmaceutically acceptable salt thereof, wherein $R^7$ is H.

7. The compound of claim 1, or a pharmaceutically acceptable salt thereof, wherein
$R^9$ and $R^{12}$ are each methyl, and $R^{10}$ and $R^{11}$ are each H, or
$R^9$, $R^{11}$, and $R^{12}$ are each methyl, and $R^{10}$ is H.

8. The compound of claim 1, or a pharmaceutically acceptable salt thereof, wherein $R^8$ is selected from $C_{16}$ alkyl, $C_{16}$ alkenyl, $C_{16}$ haloalkyl, and $C_{16}$ haloalkenyl.

9. The compound of claim 8, or a pharmaceutically acceptable salt thereof, wherein $R^8$ is $C_{16}$ alkyl or $C_{16}$ alkenyl.

10. The compound of claim 1, or a pharmaceutically acceptable salt thereof, wherein W is O.

11. The compound of claim 1, or a pharmaceutically acceptable salt thereof, wherein X is selected from β-tocopheryl, γ-tocopheryl, δ-tocopheryl, β-tocotrienyl, γ-tocotrienyl, and δ-tocotrienyl.

12. The compound of claim 1, or a pharmaceutically acceptable salt thereof, wherein X is selected from:

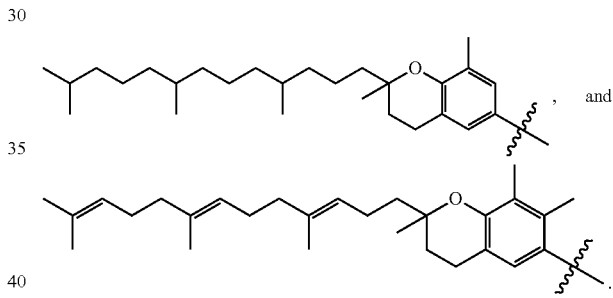

13. The compound of claim 1 selected from:

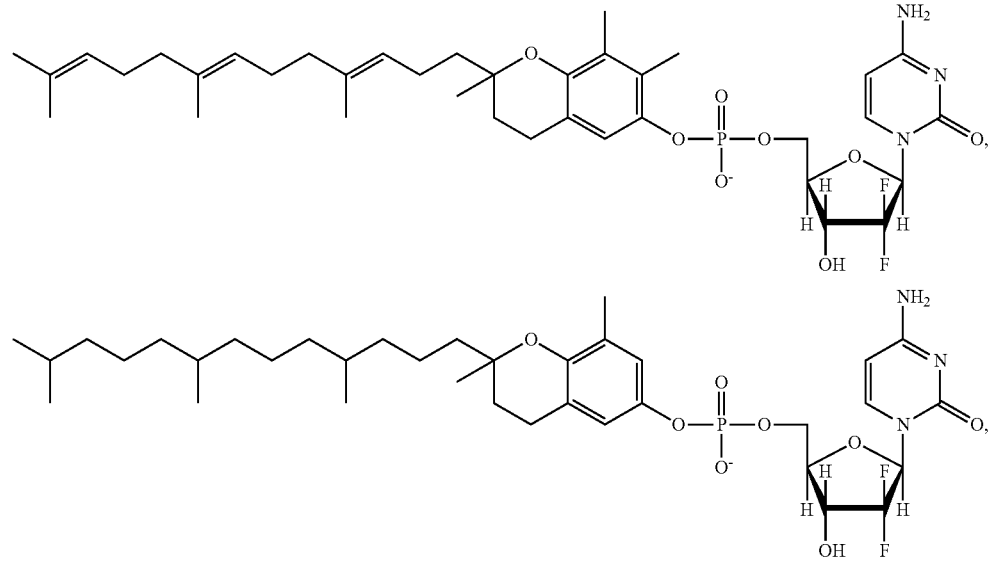

-continued

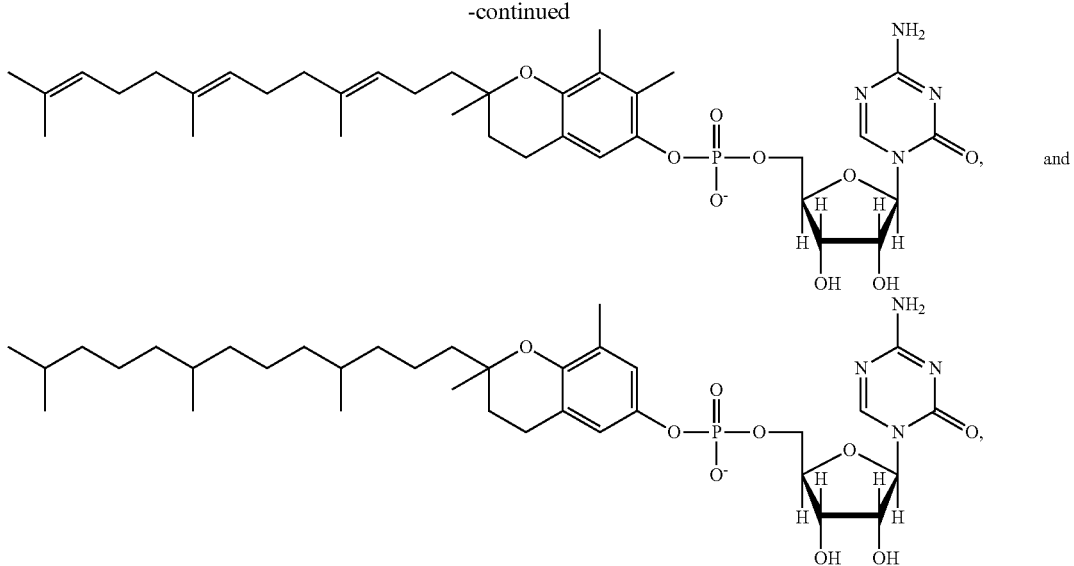

or a pharmaceutically acceptable salt thereof.

14. A method for intracellular delivery of a monophosphorylated nucleoside or nucleoside analogue, or for bypassing nucleoside transport mechanisms, comprising contacting a cell with the compound of claim 1, or a pharmaceutically acceptable salt thereof.

15. A method of treating a disease in a patient, wherein said disease is leukemia, breast, lung, or colon cancer, comprising administering to the patient a therapeutically effective amount of the compound of claim 1, or a pharmaceutically acceptable salt thereof.

* * * * *